US006015811A

United States Patent [19]
Becker et al.

[11] Patent Number: 6,015,811
[45] Date of Patent: Jan. 18, 2000

[54] ANTITUMOR CHRYSENE DERIVATIVES

[75] Inventors: Frederick F. Becker, Houston; Bimal K. Banik, Missouri City, both of Tex.

[73] Assignee: Board of Regents, The University of Texas System, Austin, Tex.

[21] Appl. No.: 09/179,513

[22] Filed: Oct. 27, 1998

[51] Int. Cl.$^7$ .......................... A61K 31/39; C07D 295/03
[52] U.S. Cl. .................................... 514/227.5; 514/237.5; 514/237.8; 514/252; 514/255; 514/319; 514/354; 514/357; 514/408; 514/423; 544/59; 544/154; 544/360; 546/195; 546/285; 548/528
[58] Field of Search .................................... 546/195, 285; 514/319, 252, 255, 237.5, 237.8, 227.5, 408, 423, 354, 357; 544/360, 154, 59; 548/528

[56] References Cited

FOREIGN PATENT DOCUMENTS 743137  9/1966  Canada .

OTHER PUBLICATIONS

Cheubim et al., "Synthesis and biological evaluation of phenathrene–derived carboxamides as cytotoxic agents," Anti–Cancer Drug Design, vol. 8, pp. 429–438 (1993).
Sami et al., "2–Substituted 1,2–Dihydro–3H–dibenz[de,h]isoquinoline–1,3–diones. A New Class of Antitumor Agent," J. Med. Chem., vol. 36, No. 6, pp. 765–770 (1993).
Yu et al., "Phenothiazines as Lipid Peroxidation Inhibitors and Cytoprotective Agents," J. Med. Chem., vol. 35, No. 4, pp. 716–724 (1992).
Leon et al., "Modulation of the Antitumor Activity by Methyl Substitutions in the Series of 7H–Pyridocarbazole Monomers and Dimers," J. Med. Chem., vol. 30, No. 11, pp. 2074–2080 (1997).
Bair et al., "2–[Arylmethyl)amino]–2–methyl–1,3–propanediol DNA Intercalators. An Examination of the Effects of Aromatic Ring Variation on Antitumor Ring Variation on Antitumor Activity and DNA Binding," J. Med. Chem., vol. 34, No. 7, pp. 1983–1990 (1991).
Nakanishi et al., "Studies of Piperidine Derivatives," J. Med. Chem., vol. 13, No. 4, pp. 644–648 (1970).
"Chrysene," Polycyclic Aromatic Hydrocarbon Structure Index, No. 39, NIST Special Publication 922 (Aug. 18, 1998).
"7H–Benzo[hi]chrysene," Polycyclic Aromatic Hydrocarbon Structure Index, No. 106, NIST Special Publication 922 (Aug. 18, 1998).
"Dibenzo[c,l]chrysene," Polycyclic Aromatic Hydrocarbon Structure Index, No. 293, NIST Special Publication 922 (Aug. 18, 1998).
"Dibenzo[c,p]chrysene," Polycyclic Aromatic Hydrocarbon Structure Index, No. 276, NIST Special Publication 922 (Aug. 18, 1998).
"Dibenzo[def,mno]chrysene," Polycyclic Aromatic Hydrocarbon Structure Index, No. 121, NIST Special Publication 922 (Aug. 18, 1998).
Derwent Abstract, "Correlations between topological resonance energy of methyl–substituted benz[c]acridines, benzo[a]phenothiazines and crysenes, and their carcinogenic or antitumor activities," Kurihara et al., Anticancer. Res., 16(5A), pp. 2757–2765 (Sep.–Oct. 1996).

Derwent Abstract, "Use of precision–cut liver slices to evaluate species differences in 2–acetylaminofluorene–induced unscheduled DNA synthesis," Lake et al., Toxicol. Appl. Pharmacol., 138 (2), pp. 231–241 (Jun. 1996).
Derwent Abstract, "Absence of mutagenicity of benzo[c]phenathridine alkaloids in somatic cells of Drosophila melanogaster: comparison with 7,12–dimethylbena[a] anthracene and crysene," Perez–Chiesa et al., Mutat. Res., 198 (4), pp. 277–283 (Feb. 1993).
Derwent Abstract, "Characterization of cytochrome P–450 2B6 in human liver microsomes," Mimura et al., Drug Metab. Dispos., 21 (6) pp. 1048–1056 (Nov.–Dec. 1993).
Derwent Abstract, "A phase II study of crisnatol mesylate in patients with ovarian carcinoma," Smalley et al., Invest. New Drugs, 10(2), pp. 107–112 (Jul. 1992).
Derwent Abstract, "An efficient multiple–exposure analysis of the toxicity of crisnatol, a DNA intercalator in phase II clinical trials," Zucker et al., Invest. New Drugs, 10 (1) pp. 1–15 (Apr. 1992).
Derwent Abstract, "New anticancer agents," Brown et al., Cancer, Chemother. Biol. Response Modif., 12, pp. 111–146 (1991).
Derwent Abstract, "Disposition, metabolism, and excretion of the anticancer agent crisnatol in the rat," Patel et al., Drug Metab. Dispos., 19 (2), pp. 491–497 (Mar.–Apr. 1991).
Derwent Abstract, "Metabolism of a novel antitumor agent, crisnatol, by a human hepatoma cell line", Patel et al., Biochem. Pharmacol., 42 (2), pp. 337–346 (Jul. 5, 1991).

(List continued on next page.)

Primary Examiner—Joseph K. McKane
Attorney, Agent, or Firm—Williams, Morgan & Amerson, P.C.

[57] ABSTRACT

Chrysene derivatives having the formula have been found to have antitumor activity. In the above formula, at least one of $R_1$–$R_{12}$ is —$R_{13}Z$, where $R_{13}$ is a substituted or unsubstituted amino or amido group having from 1–12 carbon atoms, and Z is a substituted or unsubstituted heterocyclic group having from 1–12 carbon atoms; and the remainder of $R_1$–$R_{12}$ are independently selected from the group consisting of hydrogen, substituted or unsubstituted amino or amido groups having 1–12 carbon atoms, nitro, and substituted or unsubstituted hydrocarbyl groups having from 1–12 carbon atoms.

32 Claims, 7 Drawing Sheets

OTHER PUBLICATIONS

Derwent Abstract, "Phase I evaluation of crisnatol (BWA77OU mesylate) on a monthly extended infusion schedule," Sel. Cancer Ther., 7 (2), pp. 85–91 (Summer 1991).

Derwent Abstract, "2-[(arylmethyl)amino]-2-methyl-1, 3-propanediol DNA intercalators. An examination of the effects of aromatic ring variation on antitumor activity and DNA binding," J. Med. Chem., 34 (7), pp. 1983–1990 (Jul. 1991).

Derwent Abstract, "Crisnatol mesylate: phase I dose escalation by extending infusion duration," Poplin et al., Invest. New Drugs, 9 (1), pp. 41–47 (Feb. 1991).

Derwent Abstract, "In vitro pharmacodynamic assay for cancer drug development: application to crisnatol, a new DNA intercalator," Adams, Cancer Res., 49 (23) pp. 6615–6620 (Dec. 1, 1989).

Derwent Abstract, "Phase I and clinical pharmacology trial of crisnatol (BWA77OU mesylate) using a monthly single-dose schedule," Harman et al., Cancer Res., 48 (16) pp. 4706–4710 (Aug. 15, 1988).

Derwent Abstract, WO 9422773 (Oct. 13, 1994).

Derwent Abstract, RO 91292 (Feb. 28, 1983).

Derwent Abstract, RO 79546 (Jul. 30, 1982).

Derwent Abstract, RO 75308 (Feb. 17, 1982).

Derwent Abstract, JP 57020741 (Feb. 3, 1982).

Banik et al, "A Facile Reduction of Aromatic Nitro Compounds to Aromatic Amines by Samarium and Iodine," Tetrahedron Letters, vol. 39, pp. 7243–7246 (1998).

Banik et al, "Benzylic Oxidation by Sodium Bismuthate in Acetic Acid: A Simple Method for the Synthesis of Polycyclic Aromatic Ketones," Tetrahedron Letters, vol. 39, pp. 7247–7250 (1998).

"7H–Dibenzo[c,g]fluorene," Polycyclic Aromatic Hydrocarbon Structure Index, No. 85, NIST Special Publication 922 (Aug. 17, 1998).

"13H–Dibenzo[a,i]fluorene," Polycyclic Aromatic Hydrocarbon Structure Index, No. 92, NIST Special Publication 922 (Aug. 17, 1998).

"12H–Dibenzo[b,h]fluorene," Polycyclic Aromatic Hydrocarbon Structure Index, No. 96, NIST Special Publication 922 (Aug. 17, 1998).

"7H–Dibenzo[b,g]fluorene," Polycyclic Aromatic Hydrocarbon Structure Index, No. 88, NIST Special Publication 922 (Aug. 17, 1998).

"13H–Dibenzo[a,h]fluorene," Polycyclic Aromatic Hydrocarbon Structure Index, No. 97, NIST Special Publication 922 (Aug. 17, 1998).

"13H–Dibenzo[a,g]fluorene," Polycyclic Aromatic Hydrocarbon Structure Index, No. 90, NIST Special Publication 922 (Aug. 17, 1998).

Alunni–Bistocchi et al., J. Heterocyclic Chem. 17:993–995 (1980).

Groupe Europeen du Cancer Sein, Europ. J. Cancer 3:75–77 (1967).

104a R2 = NHCO(CH2)3CON◯ , R6=H
105a R2 =H, R6 = NHCO(CH2)3CON◯ , R6=H
106a R2 = NHCOCH = CHCON◯ , R6=H
107 R2 = H, R6 = NHCOCH = CHCON◯NCH3
108b R2 = NHCOCH2CON◯NCH3 , R6=H

104b R2 = NHCO(CH2)3CON◯NCH3 , R6=H
105b R2 = H, R6=NHCO(CH2)3CON◯NCH3
106b R2 = NHCOCH=CHCON◯NCH3 , R6=H
108a R2 = NHCOCH2CON◯ , R6=H
109 R2 = NH2, R6=H    110 R2 = H, R6 = NH2

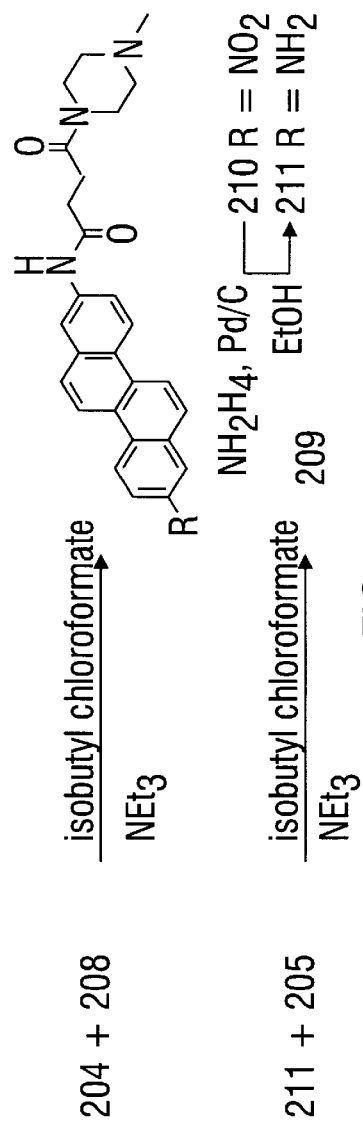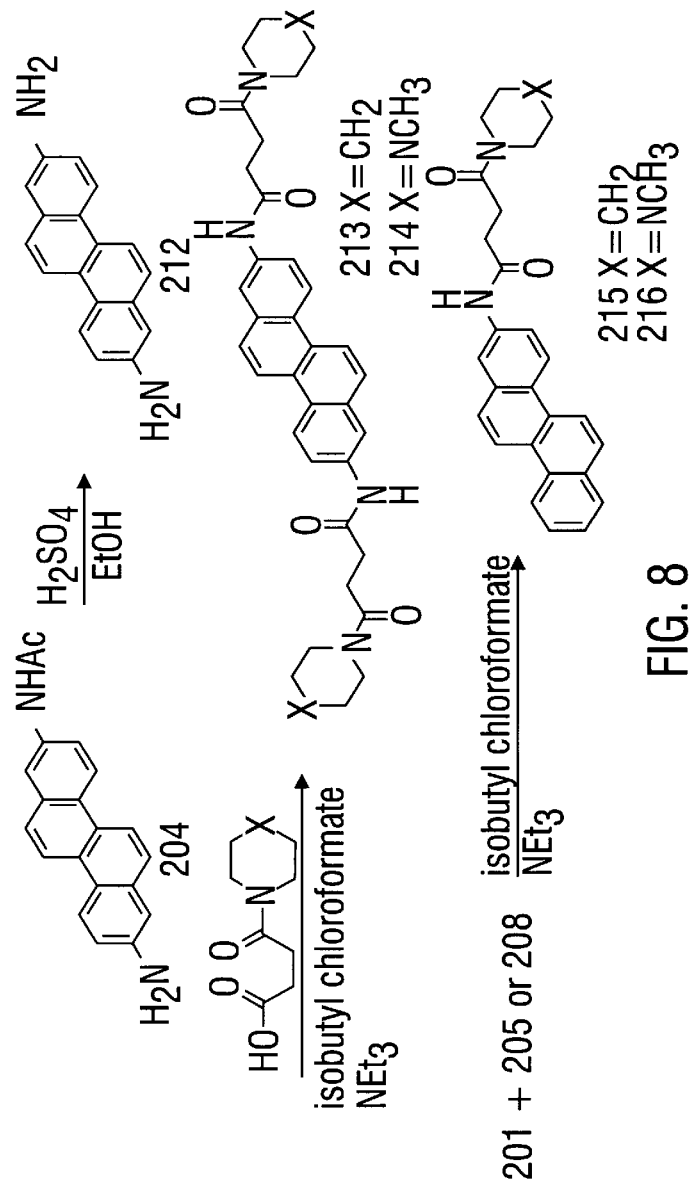
FIG. 7
FIG. 8

ANTITUMOR CHRYSENE DERIVATIVES

BACKGROUND OF THE INVENTION

The present invention relates to compounds having antitumor activity. The invention also relates to pharmaceutical compositions that contain one or more of those compounds, methods of using the compounds to inhibit tumor growth in mammals, and methods of preparing the compounds.

Many thousands of people are diagnosed with cancer each year, and although advances have been made in cancer therapy, the existing treatments are not successful in many cases. Among the problems with existing therapies are (1) anticancer drugs administered to patients often have toxic effects on non-cancerous cells in the patient's body, (2) cancerous cells whose growth can be inhibited by certain drugs sometimes become resistant to those drugs, and (3) some cancers cannot be effectively treated with a single drug, and sometimes not even with a combination of different anticancer drugs. A long-standing need exists for new anticancer drugs that have one or more of the following characteristics: (1) ability to inhibit the growth of cancerous cells, (2) acceptable levels of toxicity to non-cancerous cells, (3) effectiveness against cancerous cells that are resistant to other drugs, and (4) a different mechanism of action than existing drugs, so that when the new drug is used in combination with an existing drug, the likelihood of the cancer cells developing cross-resistance is reduced.

SUMMARY OF THE INVENTION

The present invention concerns compounds having the formula

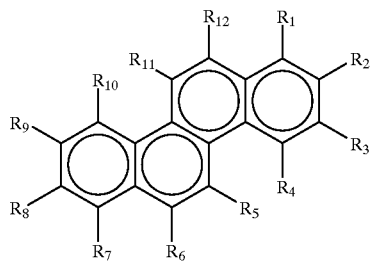

or salts of such compounds. At least one of $R_1$–$R_{12}$ is —$R_{13}Z$, where $R_{13}$ is a substituted or unsubstituted amino or amido group having from 1–12 carbon atoms, and Z is a substituted or unsubstituted heterocyclic group having from 1–12 carbon atoms. The remainder of $R_1$ –$R_{12}$ are independently selected from the group consisting of hydrogen, substituted or unsubstituted amino or amido groups having from 1–12 carbon atoms, nitro, and substituted or unsubstituted hydrocarbyl groups having from 1–12 carbon atoms.

In one embodiment of the invention, $R_2$ is —$R_{13}Z$ and $R_1$ and $R_3$–$R_{12}$ are hydrogen. In another embodiment, $R_6$ is —$R_{13}Z$ and $R_1$–$R_5$ and $R_7$–$R_{12}$ are hydrogen. In another embodiment, $R_2$ and $R_8$ are each —$R_{13}Z$ and $R_1$, $R_3$–$R_7$, and $R_9$–$R_{12}$ are hydrogen.

$R_{13}$ is preferably —$NHR_{14}$—, where $R_{14}$ is a substituted or unsubstituted aliphatic group having from 2–6 carbon atoms. $R_{14}$ is preferably selected from the group consisting of —$CO(CH_2)_nCO$—, —$(CH_2)_m$—, and —$CO(CH_2)qCHCH(CH_2)_rCO$—, where n is from 1–4, m is from 2–6, q is from 0–2, and r is from 0–2. Z as mentioned above is a substituted or unsubstituted heterocyclic group, such as piperidinyl, piperazinyl, morpholinyl, thiomorpholinyl, pyrrolidinyl, pyridinyl, thiophenyl, or derivatives thereof.

Another aspect of the present invention is pharmaceutical compositions that comprise a compound as described above and a pharmaceutically acceptable carrier. Yet another aspect of the present invention is a method of inhibiting the growth of tumor cells, in which a tumor-inhibitory amount of a compound as described above is administered to a mammal.

Another aspect of the present invention is a method of synthesizing an aromatic amino compound. This method involves reacting an aromatic compound that has a nitro group in the presence of samarium and a catalytic amount of iodine. If the aromatic compound is a chrysene derivative having a nitro group, this method can be used to synthesize antitumor chrysene derivatives as described above, or intermediates useful in the synthesis of such antitumor compounds. However, this synthetic method can also be used to prepare other aromatic amines.

The compounds and compositions of the present invention are useful in cancer therapy, either by themselves or in combination with other antitumor chemotherapy or radiation therapy.

BRIEF DESCRIPTION OF THE DRAWINGS

FIG. 6, FIG. 6A, FIG. 7, and FIG. 8 depict synthesis schemes that are described in Example 4.

DESCRIPTION OF SPECIFIC EMBODIMENTS

Figure 1:
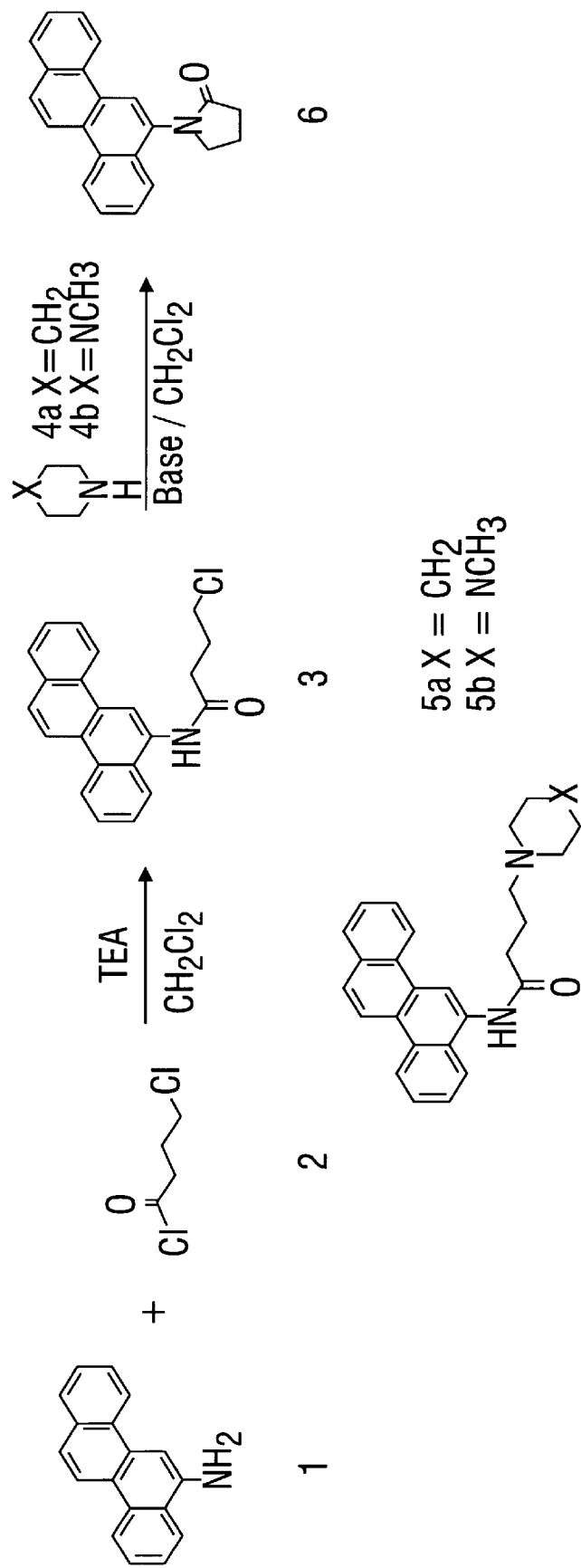
FIG. 1 and FIG. 2 depict synthesis schemes that are described in Example 1.

Polycyclic aromatic compounds are widely distributed in nature and are considered to be among the significant environmental carcinogens [1]. Previously, considerable research has been directed towards the synthesis of the polycyclic ring systems [2] and examination of their metabolic activation within target cells. Several hypotheses [3] have been proposed to establish the correlations between the structure of these metabolites, their cellular interactions and carcinogenicity. Eventually, most of the polycyclic metabolic products which act as carcinogens, intercalate with or bind covalently to DNA. Examination of several frequently used antitumor agents revealed two common structural features [4]: they have a planar ring system and a basic side chain. It could be predicted, therefore, that in addition to other cellular interactions these compounds would first demonstrate a strong interaction with the lipid domains of the plasma membranes and other membranes within the cell [5].

In some instances, antitumoral, DNA-intercalating drugs have been shown to interact with cell membranes and in some cases have demonstrated antitumor activities without further penetrating the cell structure. This then would put them in a class of drugs that have been called generically membrane stabilizing agents (MSA) [6]. These are agents which increase membrane stability against various stressors and often at higher concentration induce membrane destabilization. For example, they may act as anti-hemolytic agents at lower concentrations and cause hemolysis at higher concentrations. In order to determine the importance of these primary interactions with the plasma membrane of tumor cells in antitumor effects, we undertook an exploratory synthetic and biological evaluation of unique polycyclic aromatic compounds. This was based on our belief that the potential use of such compounds as antitumor agents has not been systematically explored [7], especially when specific modification is applied to enhance the membrane interaction as the primary effector of antitumor activity. On this basis, we began this systematic analysis by synthesizing a number of chrysene derivatives and studied their biological effects in vitro on a panel of human tumor cell lines.

A number of compounds of the present invention have been prepared, and are listed in Table 1.

TABLE 1

| Cpd No. | Compound Name |
|---|---|
| Tx-1 | N-(6'-chrysenyl)-4-(4'N methyl-piperazinyl)-butane-1,4-dicarboxiamide |
| Tx-2 | N-(2'-chrysenyl)-4-(4'N-methyl-piperazinyl)-butane-1,4-dicarboxiamide |
| Tx-3 | N-(6'-chrysenyl)-4-(1'-piperidinyl)-butane-1-4-dicarboxiamide |
| Tx-4 | N-(2'-chrysenyl)-4-(1'-piperidinyl)-butane-1,4-dicarboxiamide |
| Tx-5 | N-(2'-chrysenyl)4-(1'-piperidinyl)-butane-1,4-diamine |
| Tx-6 | N-(2'-chrysenyl)-4-(4'N methyl-piperazinyl)-butane-1,4-diamine |
| Tx-9 | N-(12'-bromo,6'-chrysenyl)-4-(4'N methyl-piperazinyl)-butane-1,4-dicarboxiamide |
| Tx-10 | N-(12'-bromo,2'-chrysenyl)-4-(4'N methyl-piperazinyl)-butane-1,4-dicarboxiamide |
| Tx-11 | N-(12'-bromo,6-chrysenyl)-4-(1'-piperidinyl)-butane-1,4-dicarboxiamide |
| Tx-12 | N-(12'-bromo,2'-chrysenyl)-4-(1'-piperidinyl)-butane-1,4-dicarboxiamide |
| Tx-13 | N-(12'-nitro,6'-chrysenyl)-4-(4'N methyl-piperazinyl)-butane-1,4-dicarboxiamide |
| Tx-14 | N-(12'-nitro,2'-chrysenyl)-4-(4'N methyl-piperazinyl)-butane-1,4-dicarboxiamide |
| Tx-15 | N-(12'-nitro,6'-chrysenyl)-4-(1'-piperidinyl)-butane-1,4-dicarboxiamide |
| Tx-16 | N-(12'-nitro,2'-chrysenyl)-4-(1'-piperidinyl)-butane-1,4-dicarboxiamide |
| Tx-17 | N-(12'-acetyl,6'-chrysenyl)-4-(4'N methyl-piperazinyl)-butane-1,4-dicarboxiamide |
| Tx-18 | N-(12'-acetyl,2'-chrysenyl)-4-(4'N methyl-piperazinyl)-butane-1,4-dicarboxiamide |
| Tx-19 | N-(12'-acetyl,6'-chrysenyl)-4-(1'-piperidinyl)-butane-1,4-dicarboxiamide |
| Tx-20 | N-(12'-acetyl,2'-chrysenyl)-4-(1'-piperidinyl)-butane-1,4-dicarboxiamide |
| Tx-21 | N-(12'-acetyl,2'-chrysenyl)-4-(4'N methyl-piperazinyl hydrochloride)-butane-1,4-dicarboxiamide |
| Tx-22 | N-(2'-chrysenyl)-4-(4'N methyl-piperazinyl hydrochloride)-butane-1,4-dicarboxiamide |
| Tx-23 | N-(6'-chrysenyl)-5-(4'N methyl-piperazinyl)-pentane-1,5-dicarboxiamide |
| Tx-24 | N-(2'-chrysenyl)-5-(4'N methyl-piperazinyl)-pentane-1,5-dicarboxiamide |
| Tx-25 | N-(6'-chrysenyl)-5-(1'-piperidinyl)-pentane-1,5-dicarboxiamide |
| Tx-26 | N-(2'-chrysenyl)-5-(1'-piperidinyl)-pentane-1,5-dicarboxiamide |
| Tx-32 | N-(2'-chrysenyl)-3-(4'N methyl-piperazinyl)-propane-1,3-dicarboxiamide |
| Tx-33 | N-(2'-chrysenyl)-3-(1'-piperidinyl)-propane-1,3-dicarboxiamide |
| Tx-36 | N-(2'-chrysenyl)-4-[1'-piperidinyl-4'-(m trifluoromethyl-phenyl)]-butane-1,4-dicarboxiamide |
| Tx-39 | N-(2'-chrysenyl)-4-(4'-morpholinyl)-butane-1,4-dicarboxiamide |
| Tx-40 | N-(2'-chrysenyl)-4-(1'-thiomorpholinyl)-butane-1,4-dicarboxiamide |
| Tx-41 | N-(2'-chrysenyl)-4-(1'-pyrrolidinyl)-butane-1,4-dicarboxiamide |
| Tx-42 | N-(6'-chrysenyl)-4-(1'-pyrrolidinyl)-butane-1,4-dicarboxiamide |
| Tx-44 | N-(2'-chrysenyl)-4-(1'-piperidinyl)-but-2-ene-1,4-dicarboxiamide |
| Tx-45 | N-(2'-chrysenyl)-4-(4'N-methyl-piperazinyl)-but-2-ene-1,4-dicarboxiamide |
| Tx-46 | N-(6'-chrysenyl)-4-(4'N-methyl-piperazinyl)-but-2-ene-1,4-dicarboxiamide |
| Tx-52 | N-(2'-chrysenyl)-4-(1'N-cycloheptanyl)-butane-1,4-dicarboxiamide |

TABLE 1-continued

| Cpd No. | Compound Name |
|---|---|
| Tx-53 | N-(6'-chrysenyl)-4-(1'N-cycloheptanyl)-butane-1,4-dicarboxiamide |
| Tx-55 | N-(2'-chrysenyl)-4-(1'N-cyclooctanyl)-butane-1,4-dicarboxiamide |
| Tx-56 | N-(6'-chrysenyl)-4-(1'N-cyclooctanyl)-butane-1,4-dicarboxiamide |
| Tx-59 | N-(2'-chrysenyl)-4-(4'N,N-dimethyl-piperizinyl iodide)-butane-1,4-dicarboxiamide |
| Tx-60 | N,N-(6',12'-chrysenyl)-bis[4-(4'N methyl-piperazinyl)-butane-1,4-dicarboxiamide] |
| Tx-61 | N-[(6'-chrysenyl)-4-(1'-piperidinyl)-butane-1,4-dicarboxiamide]-N-[(12'-chrysenyl)-4-(4'N methyl-piperazinyl)-butane-1,4-dicarboxiamide] |
| Tx-62 | N,N-(6',12'-chrysenyl)-bis[4-(1-piperidinyl)-butane-1,4-dicarboxiamide] |
| Tx-63 | N,N-(2',8'-chrysenyl)-bis[4-(4'N methyl-piperazinyl)-butane-1,4-dicarboxiamide] |
| Tx-64 | N-[(2'-chrysenyl)-4-(4'N methyl-piperazinyl)-butane-1,4-dicarboxiamide]-N-[(8'-chrysenyl)-4-(1'-piperidinyl)-butane-1,4-dicarboxiamide] |
| Tx-65 | N,N-(2',8'-chrysenyl)-bis[4-(1'-piperidinyl)-butane-1,4-dicarboxiamide] |
| Tx-70 | N-(2'-chrysenyl)-4-(4'N-methylpiperazinyl-N-oxide)-butane-1,4-dicarboxiamide |
| Tx-71 | N-(6'-chrysenyl)-4-(4'N-methylpiperazinyl-N-oxide)-butane-1,4-dicarboxiamide |
| Tx-74 | N-[(6'-chrysenyl)-4-(4'N methyl-piperazinyl)-butane-1,4-diamine]-N-[(12'-chrysenyl)-4-(1'-piperidinyl)-butane-1,4-diamine. |
| Tx-75 | N-[(2'-chrysenyl)-4-(1'-piperidinyl)-butane-1,4-diamine]-N-[(8'-chrysenyl)-4-(4'N methyl-piperazinyl)-butane-1,4-diamine |

Compounds numbered Tx-7, 8, 31, 35, 57, and 58 were prepared, but proved to be either insoluble to the extent that they could not be tested or unstable to the extent that they could not be stored appropriately.

Methods for synthesizing the compounds of the present invention are described in the examples below. Therapeutic compositions containing these compounds will preferably also include one or more pharmaceutically acceptable carriers, such as saline solution, and may also include one or more pharmaceutically acceptable excipients and/or additional biologically active substances.

The compounds of the present invention can be used in methods of inhibiting the growth of tumor cells in mammals, particularly in humans. Specific human malignancies for which these compounds should be useful include breast, colon, ovarian, and prostate cancers, melanoma, leukemia/lymphomas, and possibly others as well. The compounds are administered to a mammal in an amount effective to inhibit the growth of tumor cells in the mammal. The administration can suitably be parenteral and by intravenous, intraarterial, intramuscular, intralymphatic, intraperitoneal, subcutaneous, intrapleural, or intrathecal injection. Such administration is preferably repeated on a timed schedule until tumor regression or disappearance has been achieved, and may be used in conjunction with other forms of tumor therapy such as surgery or chemotherapy with different agents. A compound of the present invention is preferably administered in a dose that is between approximately 0.01 and 100 mg/kg of body weight of the mammalian subject. A presently preferred dosage for compound Tx-5 is between approximately 18–72 mg/kg. The present invention can be further understood from the following examples.

EXAMPLE 1

Compounds having the general structure shown below were synthesized by the schemes depicted in FIGS. 1 and 2.

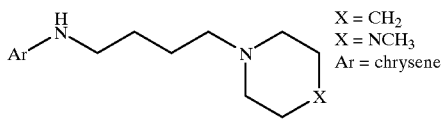

Reaction of 6-amino chrysene 1 with 4-cholorobutyryl chloride 2 in the presence of triethylamine gave the required chloroamide 3 in excellent yield. Condensation of piperidine 4a or N-methyl piperazine 4b in the presence of triethylamine or other strong bases, such as NaH and $K_2CO_3$, failed to produce the required monoamide 5. It was anticipated that the monoamide 5 would give compounds of the general structure shown above by reduction. The structure of the product was deduced to be a cyclic amide 6 formed through intramolecular cyclization (FIG. 1).

Figure 2:
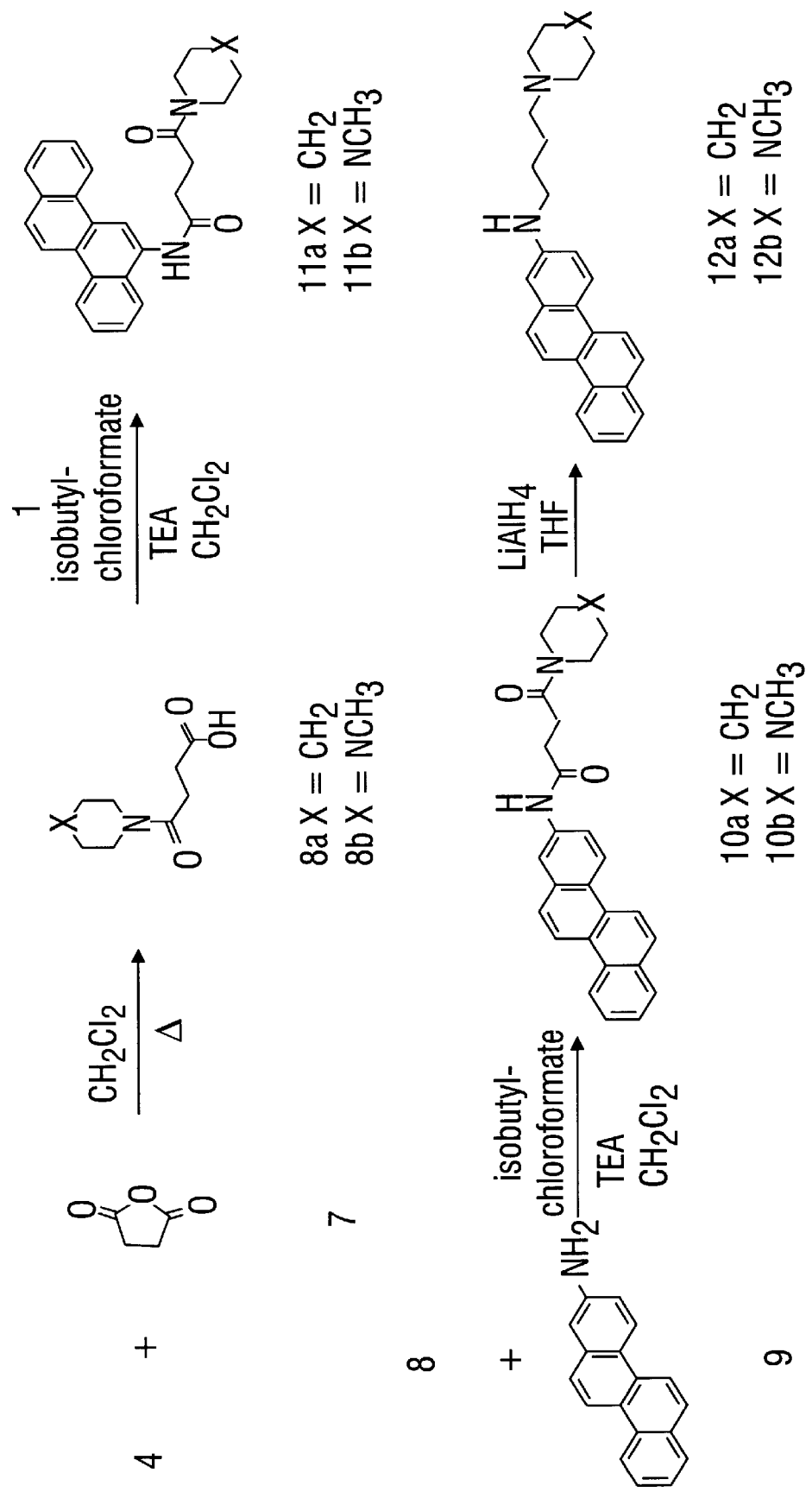

As an alternative, we prepared the acid 8 in quantitative yield by refluxing succinic anhydride 7 with piperidine 4a and N-methyl piperizine 4b using dichloromethane as solvent (FIG. 2).

Coupling reaction of the acid 8 with commercially available 2-amino chrysene 9 or 6-amino chrysene 1 with DCC [8] gave a poor yield (less than 5%) of the desired products 10 and 11 respectively. Similar reaction of the acids 8a with aniline or p-anisidine in the presence of DCC gave the amide in excellent yield indicating the difference in reactivity between polycyclic and monocyclic amines. After considerable experimentation, we discovered such coupling reaction can be carried out efficiently by isobutyl chloroformate-triethylamine method [9]. The products 10 and 11 were isolated in good yield. Reduction of the diamides 10 to the diamines 12 was carried out by $LiAlH_4$ in refluxing THF (FIG. 2).

The products were isolated by crystallization from diethyl ether or by rapid flash chromatography by using neutral alumina as adsorbent and MeOH-EtOAc (10:90) as the eluent.

The compounds of this example correlate to the listing of compounds by Tx number in Table 1 as follows:

| Compound | Compound Tx No. |
| --- | --- |
| 10a | Tx-4 |
| 10b | Tx-2 |
| 11a | Tx-3 |
| 11b | Tx-1 |
| 12a | Tx-5 |
| 12b | Tx-6 |

EXAMPLE 2

Figure 3:
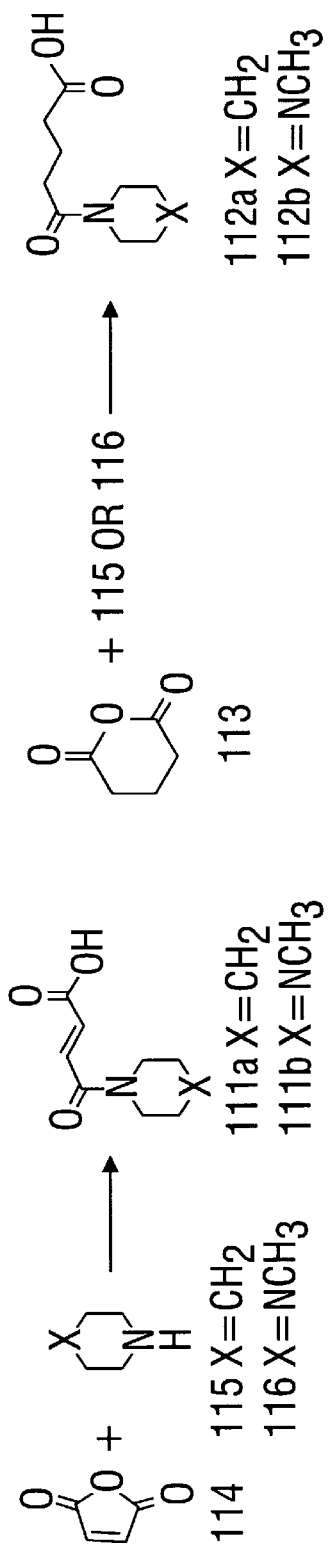
FIG. 3 and FIG. 4 depict synthesis schemes that are described in Example 2.
Figure 5:
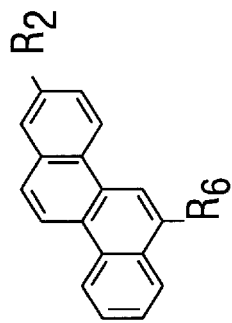
FIG. 5 shows the formula of products synthesized in Example 2.

Analogs of the compounds of Example 1 having a three or five carbon chain or unsaturated four carbon chain between the polycyclic and heterocyclic units were synthesized. The required acids, 111 and 112, for the present study were prepared in excellent yield by the direct condensation of glutaric anhydride 113 and maleic anhydride 114 with piperidine 115 or N-methylpiperazine 116 (FIG. 3). The acids 111 (obtained as the trans-isomer) and 112 were condensed with commercially available 2-amino chrysene 109 and 6-amino chrysene 110 in the presence of isobutyl-chloroformate and triethylamine [9]. The diamides 104, 105, 106, and 107 were obtained in good isolated yield (60–70%) after flash chromatography (FIG. 5). Reduction of 106a with $LiAlH_4$ gave 103a arising from the complete reduction of the diamide and unsaturated functionalities.

Figure 4:
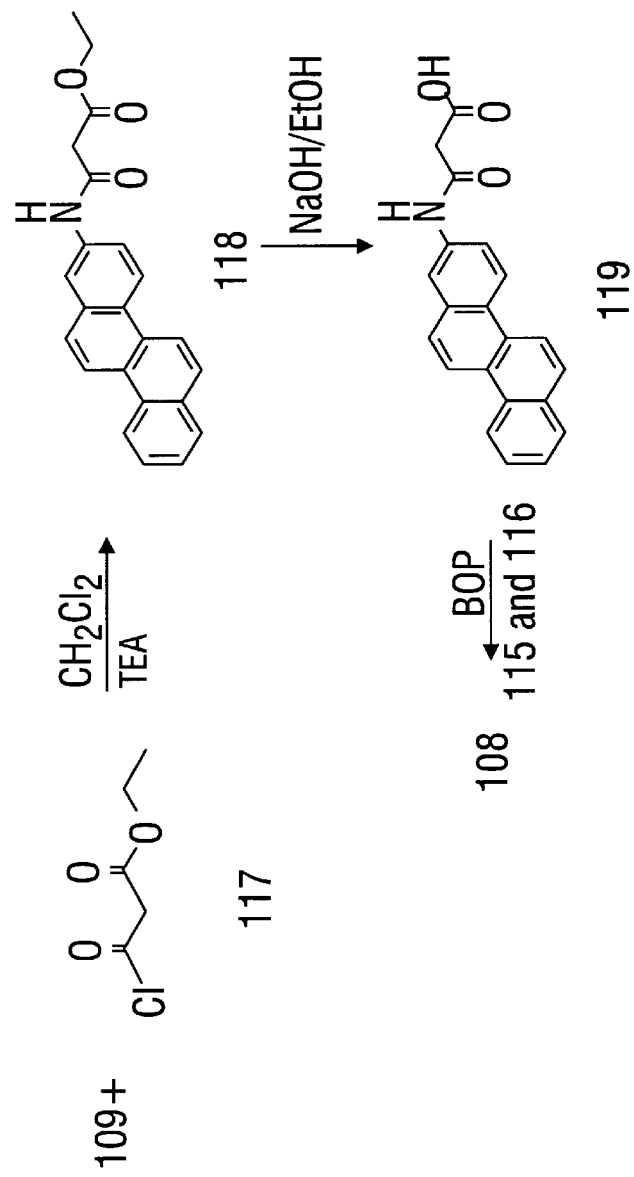

Next, we prepared two diamides 108 which have a three carbon chain in between chrysene and the heterocyclic base. Addition of ethyl malonyl chloride 117 to a solution of 2-amino chrysene 109 in dicholoromethane afforded the ethyl ester 118 which was hydrolyzed to the acid 119 by methanolic NaOH solution. Coupling reaction of the acid 119 with N-methyl piperazine 116 and piperidine 115 in the presence of isobutylchloroformate was not successful. However, the diamide 108 was obtained in good yield when BOP was used as the condensing agent [10] (FIG. 4).

The compounds of this example correlate to the listing of compounds by Tx number in Table 1 as follows:

| Compound | Compound Tx No. |
| --- | --- |
| 104a | Tx-26 |
| 104b | Tx-24 |
| 105a | Tx-25 |
| 105b | Tx-23 |
| 106a | Tx-44 |
| 106b | Tx-45 |
| 107 | Tx-46 |
| 108a | Tx-33 |
| 108b | Tx-32 |

EXAMPLE 3

As part of our experimental goal of synthesizing polycyclic compounds with anticancer properties, we became interested in developing a general synthesis of aromatic amines. Reduction of the aromatic nitro compounds by catalytic hydrogenation [11] is probably the best method known to produce the aromatic amines although various other synthesis of aromatic amines have appeared in the literature [12]. We have noted a method of reduction of the aromatic azido groups to the aromatic amines by metallic samarium [13] and iodine. One of us was previously involved in iodine catalyzed [14] reactions. We have also noted the reduction of aromatic azido compounds to amino compounds by various other methods [15]. However, aromatic azido compounds, particularly in polycyclic series are not naturally abundant, difficult to make and in some cases precaution has to be taken because of their sensitivity towards metallic objects [16]. On the other hand, aromatic nitro compounds are easily accessible by conventional nitration and many of them are commercially available. We have demonstrated a simple reduction of such compounds by samarium and iodine.

First, several monocyclic benzene derivatives were chosen for this reduction study. Thus, reduction of p-nitroanisole (reaction 1 in Table 2) to p-anisidine was achieved in refluxing methanol by samarium and catalytic amounts of iodine, as shown in the scheme below.

Scheme

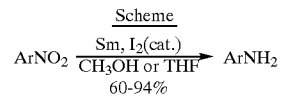

From a series of experiments we found that 4-equivalents of samarium was required for the completion of reaction. An increase in the amount of samarium did not reduce the time required. The reaction time under sonication remained the same. We found that a catalytic amount of iodine is necessary because the reduction did not proceed in the presence of samarium and methanol only. We also found that THF can be used as the solvent with equal effectiveness. Subsequently, we used several bicyclic and polycyclic nitro compounds for reduction under identical conditions and isolated the corresponding amino compounds in good yield. The results are represented in Table 2.

TABLE 2

| Reaction | Substrate | Product | Yield %[a] | Reflux Time[b] |
|---|---|---|---|---|
| 1 | 4-nitroanisole | 4-anisidine | 88 | 7 |
| 2 | 4-bromonitrobenzene | 4-bromoaniline | 86 | 3 |
| 3 | 2-nitro ethylbenzoate | 2-amino methylbenzoate | 86 | 5 |
| 4 | 1-nitronaphthalene | 1-aminonaphthalene | 64 | 8 |
| 5 | 2-nitrofluorene | 2-aminofluorene | 95 | 7 |
| 6 | 2-nitro-9-ketofluorene | 2-amino-9-ketofluorene | 60 | 6 |
| 7 | 6-nitrochrysene | 6-aminochrysene | 94 | 8 |
| 8 | 1-nitropyrene | 1-aminopyrene | 92 | 7 |
| 9 | 12-nitro-6-acetamidochrysene | 12-amino-6-acetamidochrysene | 64 | 48 |

[a]isolated yield
[b]reaction time (in hr)

The table shows some selectivity in the reduction process. Thus, there is no dehalogenation (reaction 2) or hydrogenolysis (reaction 6). The widely used catalytic hydrogenation gives dehalogenation and hydrogenolysis in most of the reactions. 2-Nitroethylbenzoate (reaction 3) gave 2-aminomethylbenzoate arising from a transesterification reaction in the presence of methanol. On the other hand, 2-aminoethylbenzoate was the product in the presence of THF.

A representative procedure is as follows: To 50 mg of the nitro compounds in 5 mL of dry methanol were added 4 equivalents of samarium and 0.1 equivalent of iodine and the mixture was refluxed under argon atmosphere until the disappearance of the starting material as indicated by TLC. The reaction mixture was diluted with 30 mL of dichloromethane and filtered. The filtrate was washed with saturated aqueous sodium thiosulfate solution and brine. The organic layer was dried over anhydrous sodium sulfate. The solvent was removed under reduced pressure and the crude product was purified by crystallization from dichloromethane-hexanes or column chromatography over basic alumina.

In order to compare the effectiveness of this samarium-induced reduction process with the well-established samarium diiodide [17] mediated reduction process, we carried out the reduction of 2-nitroflourene with 8 equivalents of samarium diiodide solution in THF and observed 80% conversion. The isolated yield from the same reaction under metal samarium-iodine induced condition is 95%. Samarium diiodide can be prepared by refluxing overnight equimolar samarium and iodine in THF [18]. As can be seen from the table, the reduction of several nitro compounds was completed within 3–8 h although we used catalytic amounts of iodine. Thus, we suggest that freshly prepared reducing agent from samarium and catalytic amounts of iodine is a better reagent than commercially available samarium diiodide. Samarium diiodide is available in sealed bottle but can be inactivated even after a brief exposure to moisture. As a result, we required different amounts of samarium iodide-THF solution for the reduction of the same nitro compound under identical conditions from a bottle which we used at a one month interval. The high reactivity of the metallic samarium is probably a result of the high reducing power as shown by the reduction potential data [13] ($Sm^{3+}/Sm=-2.41V$ vs $Sm^{3+}/SM^{2+}=-1.55V$.

Use of some salts and Lewis acids [19] in some cases produced hydroxyl amine derivatives under samarium-iodine induced reduction conditions. Prolonged reaction time or drastic conditions did not alter the product distribution. However, no hydroxyl amine derivatives were observed in the present reduction method by samarium-iodine. The intermediates, if any, may be transformed to the final amines very rapidly without building sufficient concentration.

In conclusion, we have shown a simple method for the reduction of the aromatic nitro compounds to the amines in excellent yield. (All products were characterized through a comparison of mp, TLC, and NMR with authentic compounds.) Some of the polycyclic amines that we have synthesized are versatile starting materials for the development of anticancer agents. [20]

EXAMPLE 4

As part of our study on the synthesis and biological evaluation of polycyclic aromatic compounds as anticancer agents, we have found that some 2-substituted chrysene derivatives are more potent than the corresponding 6-isomers. In order to investigate the 2-substituted chrysene derivatives in a highly functionalized system, electrophilic substitution reaction of the polycyclic system is necessary. This example describes the nitration of 2-acetamidochrysene and synthesis of some 2,8-disubstituted chrysene compounds.

Electrophilic aromatic substitution reaction is an important synthetic reaction [21]. The orientation of the electrophile in simple benzene and naphthalene derivatives is predictable in most of the cases. On the other hand, electrophilic reaction in polycyclic aromatic system is difficult to achieve and there is no clear orientation rule. In the past, most of the research in polycyclic aromatic systems was directed towards the synthesis of the ring system [22] and to define the mechanism of their carcinogenicity [23]. We have noted nitration and bromination studies of 6-acetamidochrysene in the literature [24]. The orientation of the nitro and bromo group in 6-acetamidochrysene was determined by chemical correlation study.

Figure 6:
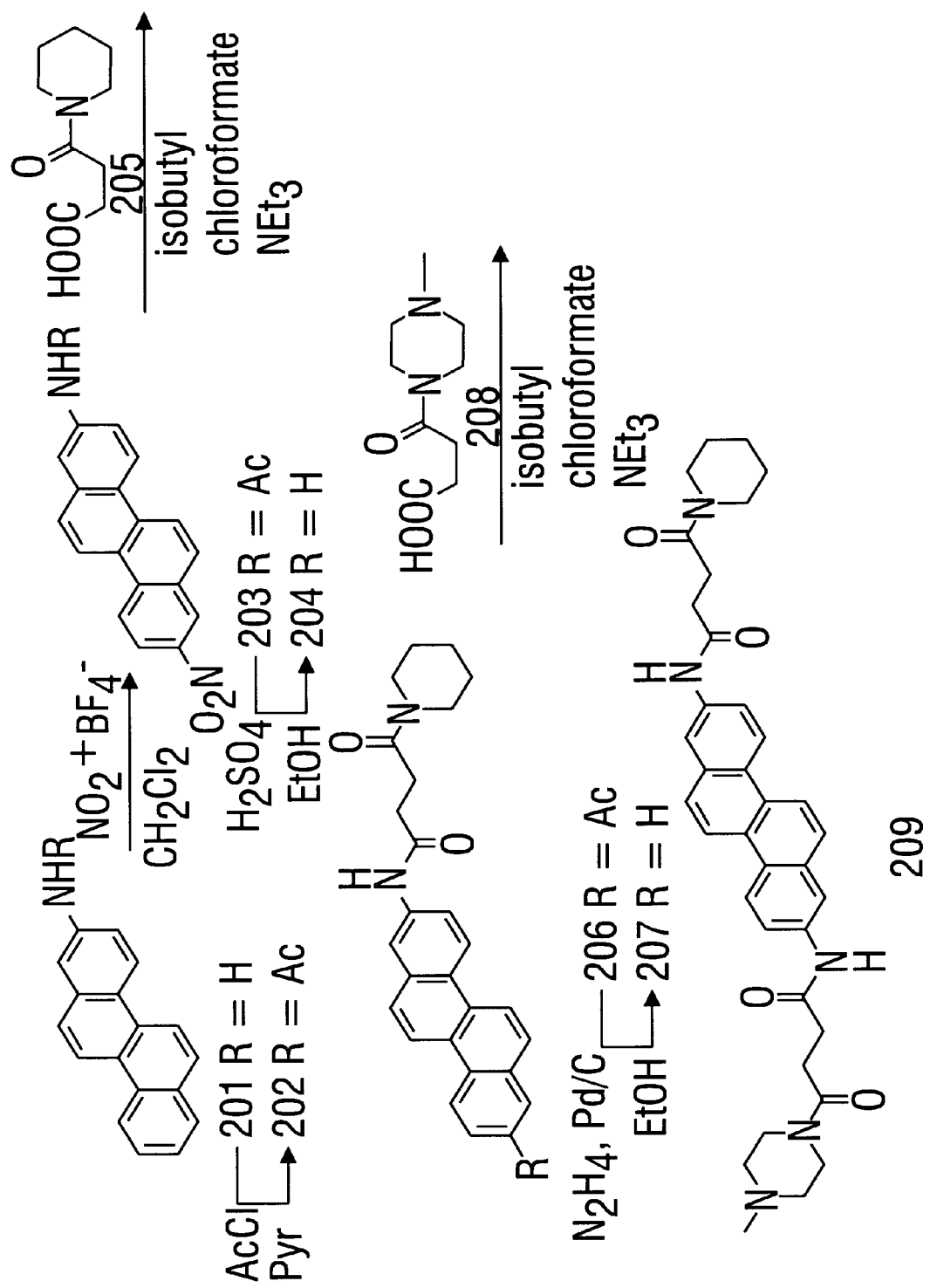

As shown in FIG. 6, 2-acetamidochrysene 202, prepared by the acetylation of commercially available 2-amino chrysene 201, after nitration with nitronium tetrafluroborate [25] as the nitrating agent gave a single nitro derivative 203. The product was purified by crystallization and on the basis of NMR, substitution at the 8-position was indicated. In order to confirm the position of electrophilic attack, the nitro compound 203 was subjected to hydrolysis to provide the amine 204. Condensation of the amine 204 with the side chain 205 (prepared earlier) via the mixed anhydride method furnished the nitro diamide 206 in 82% yield. Catalytic transfer hydrogenation [26, 27] of the nitro diamide 206 gave amino diamide 207 which on condensation with acid 208 produced tetramide 209 with two dissimilar side groups on the aromatic ring. It was reasoned that if the site of electrophilic attack was at position 8, reversal of condensation steps should produce the same tetramide 209 due to the symmetrical nature of the molecule (FIG. 6).

Figure 6A:
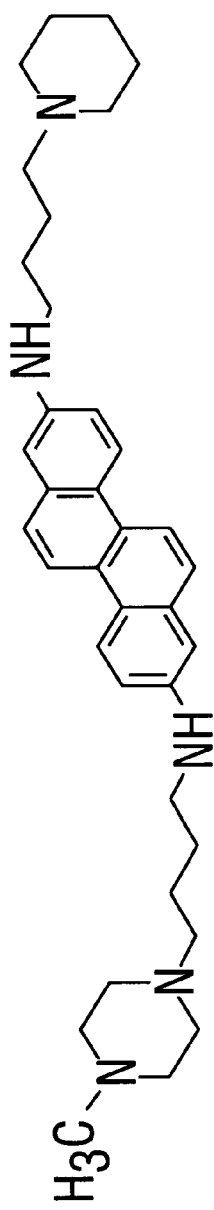
Figure 6A:
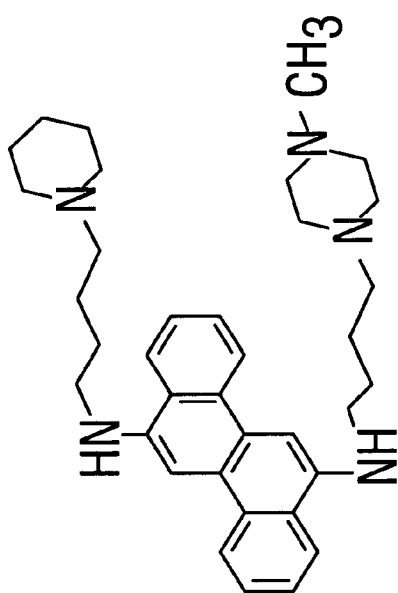

Reduction of the tetra-amide 209 produced the tetra-amine 210 in excellent yield. By following an identical sequence described above, 6–12 disubstituted tetra-amine 211 was prepared (FIG. 6A).

Thus, coupling reaction of N-methyl piperazine containing side chain 208 with 204 was performed and the resulting product 210 was reduced to the amine 211 under transfer hydrogenation conditions. Condensation of the amine 211 with the piperidine containing side chain 205 gave tetramide 209. The identical physico-chemical properties of the tetramide 209 prepared by two different routes confirmed a symmetrical product which in this case is only possible if the electrophilic attack takes place at 8-position (FIG. 7).

With site of electrophilic attack confirmed, it was decided to prepare two C-2 symmetric compounds 213 and 214. Thus, diamine 212 obtained by the hydrolysis of 204 was condensed with the side chains 205 and 208. The products 213 and 214 were isolated in good yield. (FIG. 8).

The compounds of this example correlate to the listing of compounds by Tx number in Table 1 as follows:

| Compound | Compound Tx No. |
|---|---|
| 206 | Tx-16 |
| 209 | Tx-64 |
| 210 | Tx-14 |
| 213 | Tx-65 |
| 214 | Tx-63 |
| 215 | Tx-4 |
| 216 | Tx-2 |

EXAMPLE 5

Chrysene In Vitro Cytotoxicity Testing

Chrysene derivatives were tested, as will be described below, against six to eight cultured, tumor cell lines of human and/or animal origin, at least half of which were selected from the NCI panel of test tumors. In each experiment, Adriamycin (ADR) was used as a maximally positive control. Subsequent to our determination that the chrysene derivative Tx-2 demonstrated remarkably consistent, relatively positive effects, it was also included in the panel of test agents in every experiment where chrysene analogs were tested. No cytotoxicity data is given in Table 3 for some of the Tx numbers because they proved to be totally insoluble in any reasonable solvent combination and therefore were not included in the testing pattern.

In Vitro Cytotoxicity Determinations

Data are $IC_{50}$ values (MTT assay) reported as μg/ml for 72 hours continuous exposure to the drug. Drugs were prepared in DMSO:PEG300 (1:1). Further, dilutions were made in a cell culture medium with fetal bovine serum.

Test Tumor Lines

| | |
|---|---|
| BRO | human melanoma |
| HT-29 | human colon adenocarcinoma |
| p388/0 | murine lymphatic leukemia |
| MCF-7 | human breast carcinoma |
| HL-60 | human promyelocytic leukemia |
| OVCAR 3 | human ovarian carcinoma |

Additional tumor lines against which the drugs were tested in certain series included L1210 (leukemia), PC3 (prostate) and several others.

Compounds were evaluated for solubility characteristics in vehicles which would be appropriate for use in cell culture. The compounds were added to the cell lines under continuous culture for 72 hours. Inhibition of growth relative to control cell culture was determined by the MTT method at the end of 72 hours. This is a test of the relative ability of a compound to inhibit cell growth not survival. However, inhibition of growth may reflect cell death and/or cytostasis.

Summarized results of the in vitro cytotoxicity testing, specifically average $IC_{50}$ values for the various tumor lines, are given in Table 3.

TABLE 3

| Agent | # Runs | P388/0 | BRO | HT-29 | MCF-7 | OVCAR-3 | HL-60 |
|---|---|---|---|---|---|---|---|
| ADR | 23 | 0.24 | 0.29 | 0.44 | 0.31 | 0.10 | 0.22 |
| Tx-1 | 3 | 8.5 | 13.5 | 6.3 | 11.2 | 7.0 | |
| Tx-2 | 17 | 7.5 | 8.9 | 6.5 | 9.7 | 8.7 | 5.9 |
| Tx-3 | 2 | 13.0 | 23.2 | 15.2 | 11.5 | | |
| Tx-4 | 3 | 20.2 | >50 | 15.7 | 19.6 | | >50 |
| Tx-5 | 3 | 2.2 | 3.2 | 2.3 | 4.1 | | 3.8 |
| Tx-6 | 2 | 4.7 | 8.8 | 9.3 | 12.1 | | 8.7 |
| Tx-9 | 1 | >50 | >50 | >50 | >50 | >50 | |
| Tx-10 | 1 | 9.9 | 37.3 | 13 | >50 | 38.1 | |
| Tx-11 | 1 | >50 | >50 | >50 | 29.2 | 11.8 | |
| Tx-12 | 1 | >50 | 43.4 | >50 | >50 | >50 | |
| Tx-13 | 1 | 4.9 | 23.4 | 13.7 | 51.3 | 10.8 | |
| Tx-14 | 1 | 2.2 | 55.5 | 21.2 | 55.1 | 11.1 | |
| Tx-15 | 1 | 7.4 | 20.2 | 6.1 | 42.8 | 9.8 | |
| Tx-16 | 1 | 3.1 | 13.2 | 6.3 | 24.6 | 12.9 | |
| Tx-17 | 1 | >100 | >100 | 88.5 | >100 | >100 | |
| Tx-18 | 2 | 53.5 | 16.4 | 48.4 | 33.0 | 19.7 | 7.1 |
| Tx-19 | 1 | | 6.3 | 42.5 | 70.8 | >100 | |
| Tx-20 | 1 | | 8.6 | 63.1 | 74.1 | >100 | |
| Tx-21 | 1 | 9.2 | 18.6 | 17.7 | 26.2 | 27.2 | |

TABLE 3-continued

| Agent | # Runs | P388/0 | BRO | HT-29 | MCF-7 | OVCAR-3 | HL-60 |
|---|---|---|---|---|---|---|---|
| Tx-22 | 3 | 4.5 | 7.5 | 9.0 | 15.9 | 12.8 | 7.7 |
| Tx-23 | 1 | 6.5 | 11.3 | 7.9 | 13.9 | 5.6 | |
| Tx-24 | 2 | 6.2 | 9 | 8.1 | 11.7 | 9.7 | |
| Tx-25 | 1 | 70.9 | 39.5 | 94.8 | 23.8 | 38.3 | |
| Tx-26 | 1 | 78.9 | 43.9 | >100 | 41.6 | 29.2 | |
| Tx-32 | 1 | 6.5 | 9.9 | 13 | 6.0 | 12.2 | |
| Tx-36 | 1 | 11.6 | 6.3 | 16.4 | 6.0 | 19.8 | |
| Tx-39 | 1 | 7.1 | 24.9 | 20.9 | 51.1 | | 6.1 |
| Tx-40 | 1 | 9.2 | 59.3 | 24.4 | 55.3 | 3.4 | 5.0 |
| Tx-41 | 1 | 15.9 | 45.6 | 7.1 | 15.9 | 7.2 | 6.2 |
| Tx-42 | 1 | 57.7 | 87.5 | 44.7 | 45.7 | 13.0 | 14.7 |
| Tx-44 | 1 | 5.9 | 19.0 | 6.5 | 6.3 | 6.8 | 4.8 |
| Tx-45 | 2 | 7.9 | 10.1 | 6.2 | 6.2 | 7.1 | 3.9 |
| Tx-46 | 1 | 7.0 | 11.5 | 5.3 | 6.5 | 5.3 | 6.9 |
| Tx-52 | 1 | 18.5 | 24 | | 7.2 | | 3.7 |
| Tx-55 | 1 | 19.9 | 44.6 | | 4.9 | | 4.5 |
| Tx-56 | 1 | 95.3 | 33.4 | | 39.6 | 49.5 | 10.3 |
| Tx-59 | 1 | 55.3 | 54.8 | | 26.6 | 21.0 | 32.0 |
| Tx-60 | 1 | 83.6 | 56 | | 45.8 | 45.6 | >100 |
| Tx-61 | 2 | 13.2 | 14.9 | | 6.1 | 10.1 | 5.1 |
| Tx-62 | 1 | 64.6 | 22.9 | | 11.3 | 20.4 | 22.5 |
| Tx-63 | 1 | 35.7 | 61.9 | | 16.3 | 29.9 | 13.4 |
| Tx-64 | 1 | 19.5 | 13.9 | | 6.2 | 8.4 | 5.3 |
| Tx-65 | 1 | 48.8 | 47.1 | | 13.4 | 27.6 | 16.1 |
| Tx-70 | 1 | 58.7 | 55.7 | 6.3 | 23.4 | 47.3 | |
| Tx-71 | 1 | 59.3 | 55.6 | 59.6 | 30.2 | 43.4 | |
| Tx-74 | 2 | 1.9 | 1.5 | 1.3 | 1.5 | 1.3 | |
| Tx-75 | 1 | 1.9 | 2.3 | 1.4 | 1.5 | 1.3 | |

An $IC_{50}$ value above 50 μg/ml indicates that there was insufficient cytotoxicity of the compound to achieve a 50% inhibition of cell growth at 50 μg/ml. In some cases, we observed cytotoxicity at 100 μg/ml but few of the drugs are readily soluble at this concentration and the data are not reliable.

ADR invariably produced the described anti-tumor effect against all tumor lines at concentrations lower than 1 μg/ml of culture media. The effect of the Tx- compounds was divided into five activity groups as described below. In all cases, if activity against a single tumor line differed radically from that against all others, notation was made of this specificity but the agent was grouped as determined by the majority of the results.

Group A. These agents were effective against all tumor lines at concentrations under 5 μg/ml. Some of these compounds were effective at less than 1 log difference from the activity of ADR.

Group B. These agents were effective against all tumor lines at less than 10 μg/ml.

Group C. These agents were effective against one-third to one-half of all tumor lines tested at levels less than 10 μg/ml.

Group D. These agents were effective against one or two of the six to eight tumor lines tested at concentrations of less than 10 μg/ml.

Group E. These agents produced some anti-tumor effect at doses above 10 μg/ml but less than 20 μg/ml.

Group F. These agents were "effective" against some tumor lines above 20 μg/ml but often demonstrated little or no anti-tumor effect.

TABLE 4

| Group A | |
|---|---|
| Tx-5 | Tx-75 |
| Tx-74 | |
| Group B | |
| Tx-2 | Tx-44 |
| Tx-6 | Tx-45 |
| Tx-22 | Tx-46 |
| Tx-32 | |
| Group C | |
| Tx-1 | Tx-40 |
| Tx-23 | Tx-41 |
| Tx-24 | Tx-64 |
| Tx-39 | |
| Group D | |
| Tx-15 | Tx-52 |
| Tx-16 | Tx-55 |
| Tx-20 | Tx-61 |
| Tx-36 | |
| Group E | |
| Tx-3 | Tx-42 |
| Tx-13 | |
| Tx-14 | Tx-62 |
| Tx-18 | Tx-63 |
| Tx-19 | Tx-65 |
| Tx-21 | |
| Group F | |
| Tx-4 | Tx-25 |
| Tx-9 | Tx-26 |
| Tx-10 | Tx-56 |
| Tx-11 | Tx-59 |
| Tx-12 | Tx-60 |
| Tx-17 | Tx-70 |
| | Tx-71 |

In summary of these findings, the most active compounds produced in this series were Tx-5, the diamine derivative of Tx-4, and Tx-74 and Tx-75, the asymmetrical bis tetra-amine derivatives of chrysene. The use of the term "asymmetrical" in this instance refers to the presence of two dissimilar terminal heterocylic molecules. Tx-2 and a number of its derivatives including the diamine (TX-6); hydrochloride salt (Tx-22); and alkyl chain variations in which the chain length was modified (TX-32) or an unsaturated group (Tx-45) inserted were equally active against all tumor lines. However, the insertion of an unsaturated group in the alkyl chains of Tx-1 and Tx-4 produced modest increase in activity in the former (Tx-46) and significant increase in activity in the latter (Tx-44).

As has been the case in other compounds based on other polycyclic ring structures, those that terminate in a piperazine ring demonstrated far greater activity than those that terminated in a piperidine ring. Thus, Tx-2 and Tx-1 demonstrated greater anti-tumor activity than did Tx-4 and Tx-3. Modification of other components of the molecule, however, such as reduction of the amides to diamines, may alter this relationship between heterocyclic rings significantly, as seen with Tx-5 and Tx-4.

Although other analogs of these four showed significant activity against selected tumor lines, none presented the overall effectiveness of the Group A and B agents.

The preceding description of specific embodiments of the present invention is not intended to be a complete list of every possible embodiment of the invention. Persons skilled in this field will recognize that modifications can be made to the specific embodiments described here that would be within the scope of the present invention.

REFERENCES

The following references, to the extent that they provide exemplary procedural or other details supplementary to those set forth herein, are specifically incorporated herein by reference.

[1] For a general review see: Freudenthal R, Jones P W. Carcinogenesis—a comprehensive survey. New York: Raven Press, 1976; vol.1–3.
[2] For a recent example see: Harvey R G. Polycyclic aromatic hydrocarbons. Wiley-VCH, 1997.
[3] Di Raddo P, Chan T H. J. Org. Chem. 1982;47:1427 and references cited therein.
[4] For some recent examples: (a) Cherubim P, Deady L W, Dorkos M, Quazi N H, Baguley B C, Denny W A. Anti-cancer drug design. 1993;8:429. (b) Palmer B D, Lee H H, Baguley B C, Denny W A. J. Med. Chem. 1992;35:258. (c) Atwell G J, Rewcastle G W, Baguley B C, Denny W A. J. Med. Chem. 1987;30:664 and references cited therein.
[5] Wingard L B, Tritton T R. Cancer Res. 1985;45:3529.
[6] (a) Jorgensen K, Ipsen J H. Biochem. Biophys. Acta. 1991;1062:227. (b) Kanaho Y, Sato T. Mol. Pharm. 1981; 20:704.
[7] Bair K W, Tuttle R L, Knick V C, Cory M, McKee D D. J. Med. Chem. 1990;33:2385.
[8] Lee M, Lown J W. J. Org. Chem. 1987;52:5717.
[9] Holzapfel C W, Pettit GR. J. Org. Chem. 1985;50:2323.
[10] Jensen-Hoeg T, Jakobsen, M H, Hclm A. Tetrahedron Lett. 1991, 32, 6387.
[11] For catalytic heterogenous hydrogenation, see: (a) Rylander, P. N. *Hydrogenation Methods*; Academic Press: New York, 1985; Chapter 8. (b) Johnstone, R. A. W.; Wilby, A. H.; Entistle, I. D. *Chem. Rev.* 1985, 85, 129. (c) Weir, J. R.; Patel, B. A.; Heck, R. F. *J. Org. Chem.* 1980, 45, 4926. (d) Tafesh, A. M.; Beller, M. *Tetrahedron Lett.* 1995, 36, 9305. For catalytic homogeneous hydrogenation, see: (a) James, B. R. *Homogeneous Hydrogenation*, Wiley: New York, 1973. (b) Greenspoon, N.; Keinan, E. *J. Org Chem.* 1988, 53, 3723. For catalytic transfer hydrogenation, see: (a) Weiner, H.; Blum, J.; Sasson, Y. *J. Org. Chem.* 1991, 56, 4481. (b) Rajagopal, S.; Spatola, A. F. J. Org. Chem. 1995,56,4481.
[12] For example, see: (a) Coleman G. H.; Blomquist, R. F. *J. Am. Chem. Soc.* 1941, 63, 1692. (b) Beak, P.; Kokko, B. *J. Org. Chem.* 1982, 47, 2822. (c) Kokko B.; Beak P. *Tetrahedron Lett.* 1983, 24, 561. (d) Beak, P. Basha A.; Kokko, B.; Loo, B. *J. Am. Chem. Soc.* 1986, 108, 6016. (e) Guram, A. S.; Buchwald, S. L. *Angew. Chem. Int. Ed. Engl.* 1995, 34, 1348. (f) Louie, J.; Hartwig, J. F. *Tetrahedron Lett.* 1995, 36, 3609. (g) Wolfe, J. P.; Buchwald, S. L. *J. Org. Chem.* 1996, 61, 1133.
[13] Huang, Y.; Zhang, Y.; Wang, Y. *Tetrahedron Lett.* 1997, 38, 1065.
[14] (a) Banik, B. K.; Manhas, M. S.; Bose, A. K. *J. Org Chem.* 1994, 59, 4714. (b) Banik B. K.; Manhas, M. S.; Bose, A. K. *Tetrahedron Lett.* 1997, 38, 5077. (c) Banik, B. K.; Zegrocka, O.; Manhas, M. S.; Bose, A. K. *Heterocycles* 1997, 46, 173.
[15] For some recent examples: (a) Scriven, E. F. V.; Turnbull, K. *Chem Rev.* 1988, 88, 297. (b) Benati, L.; Montevecci, P. C.; Nanni, D.; Spagnolo, P.; Volta, M. *Tetrahedron Lett.* 1995, 36, 7313. (c) Goulaouic- Dubois, C.; Hesse, M. *Tetrahedron Lett.* 1995, 36, 7427. (d) Capperucci, A.; Degl'Innocenti, A.; Funicello, M.; Mauriello, G.; Scafato, P.; Spagnolo, P. *J. Org. Chem.* 1995, 60, 2254. (e) Baruah, M.; Boruah, A.; Prajapati, D.; Sandhu, J. S. *Synlett* 1996, 1193. (f) Kabalka, G.; Li G. *Tetrahedron Lett.* 1997, 38, 5777. (g) Hays, D. S.; Fu, G. C. *J. Org. Chem.* 1998, 63, 2796.
[16] The explosion of azides in the presence of metal catalysts is reported, for example, see: Sanler, S. R. *Organic Functional Group Preparation*, Vol, Academic Press Inc. 1992; chapter 13.
[17] For some recent examples, see: (a) Molander, G. A. *Chem. Rev.* 1992, 92, 29. (b) Hasegawa, E.; Curran, D. P. *J. Org. Chem.* 1993, 58, 5008. (c) Molander, G. A.; Harris, C. R. *Chem. Rev.* 1996, 6, 307.
[18] Imamoto, T.; Ono, M. *Chem. Lett.* 1987, 501.
[19] Hou, Z.; Fujiwara, Y.; Hiroshi, T. *J. Org. Chem.* 1988, 53, 3118.
[20] Rudali, G.; Buu-Hoi, N. P.; Lacassagne, A. *C. R. Acad. Sci.(Paris)* 1953, 236, 2020.
[21] Hoggett, Moodie, Penton, Schofeld, "Nitration and Aromatic Reactivity" pp. 122–145, Cambridge University Press, London, 1971; Ferguson, Chem Rev. 1952;50: 47.
[22] For example, see: Harvey R G. Polycyclic aromatic hydrocarbons. Wiley-VCH, 1997
[23] Di Raddo P; Chan T H. J. Org. Chem. 1982;47:1427 and references cited therein
[24] Buu-Hoi, J. Org. Chem. 1954;19:721; Buu-Hoi, N. P. J. Org. Chem. 1954, 1396.
[25] Olah, GA. *J Am. Chem Soc.* 1962;84:3684.
[26] Weiner, H.; Blum, J.; Sasson, Y. *J. Org. Chem.* 1991;56:4481.
[27] Rajagopal, S.; Spatola, AF. *J. Org. Chem.* 1995; 56: 4481.

What is claimed is:

1. A compound having the formula

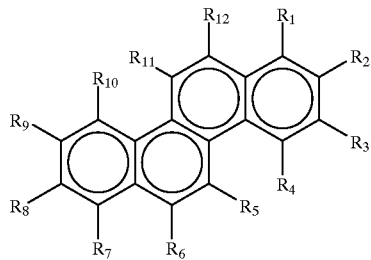

or a salt thereof;
where at least one of $R_1$–$R_{12}$ is —$R_{13}Z$, where $R_{13}$ is a substituted or unsubstituted amino or amido group having from 1–12 carbon atoms, and Z is a substituted or unsubstituted heterocyclic group having from 1–12 carbon atoms; and
where the remainder of $R_1$–$R_{12}$ are independently selected from the group consisting of hydrogen, substituted or unsubstituted amino or amido groups having from 1–12 carbon atoms, nitro, and substituted or unsubstituted hydrocarbyl groups having from 1–12 carbon atoms.

2. The compound of claim 1, where $R_2$ is —$R_{13}Z$ and $R_1$ and $R_3$–$R_{12}$ are hydrogen.

3. The compound of claim 1, where $R_6$ is —$R_{13}Z$ and $R_1$–$R_5$ and $R_7$–$R_{12}$ are hydrogen.

4. The compound of claim 1, where $R_2$ and $R_8$ are each —$R_{13}Z$ and $R_1$, $R_3$–$R_7$, and $R_9$–$R_{12}$ are hydrogen.

5. The compound of claim 1, where $R_{13}$ has the formula —$NHR_{14}$—, where $R_{14}$ is a substituted or unsubstituted aliphatic group having from 2–6 carbon atoms.

6. The compound of claim 5, where $R_{14}$ is selected from the group consisting of —$CO(CH_2)_nCO$—, —$(CH_2)_m$—, and —$CO(CH_2)_qCHCH(CH_2)_rCO$—, where n is from 1–4, m is from 2–6, q is from 0–2, and r is from 0–2.

7. The compound of claim 1, where Z is selected from the group consisting of piperidinyl, piperazinyl, morpholinyl, thiomorpholinyl, pyrrolidinyl, pyridinyl, and thiophenyl.

8. The compound of claim 1, where the compound is selected from the group consisting of:
N-(2'-chrysenyl)4-(1'-piperidinyl)-butane-1,4-diamine;
N-[(6'-chrysenyl)-4-(4'N methyl-piperazinyl)-butane-1,4-diamine]-N-[(12'-chrysenyl)-4-(1'-piperidinyl)-butane-1,4-diamine; and
N-[(2'-chrysenyl)-4-(1'-piperidinyl)-butane-1,4-diamine]-N-[(8'-chrysenyl)-4-(4'N methyl-piperazinyl)-butane-1,4-diamine.

9. The compound of claim 1, where the compound is selected from the group consisting of:
N-(2'-chrysenyl)-4-(4'N-methyl-piperazinyl)-butane-1,4-dicarboxiamide;
N-(2'-chrysenyl)-4-(4'N methyl-piperazinyl)-butane-1,4-diamine;
N-(2'-chrysenyl)-4-(4'N methyl-piperazinyl hydrochloride)-butane-1,4-dicarboxiamide;
N-(2'-chrysenyl)-3-(4'N methyl-piperazinyl)-propane-1,3-dicarboxiamide;
N-(2'-chrysenyl)-4-(1'-piperidinyl)-but-2-ene-1,4-dicarboxiamide;
N-(2'-chrysenyl)-4-(4'N-methyl-piperazinyl)-but-2-ene-1,4-dicarboxiamide; and
N-(6'-chrysenyl)-4-(4'N-methyl-piperazinyl)-but-2-ene-1,4-dicarboxiamide.

10. The compound of claim 1, where the compound is selected from the group consisting of:
N-(6'-chrysenyl)-4-(4'N methyl-piperazinyl)-butane-1,4-dicarboxiamide;
N-(6'-chrysenyl)-5-(4'N methyl-piperazinyl)-pentane-1,5-dicarboxiamide;
N-(2'-chrysenyl)-4-(4'-morpholinyl)-butane-1,4-dicarboxiamide;
N-(2'-chrysenyl)-4-(1'-thiomorpholinyl)-butane-1,4-dicarboxiamide;
N-(2'-chrysenyl)-4-(1'-pyrrolidinyl)-butane-1,4-dicarboxiamide; and
N-[(2'-chrysenyl)-4-(4'N methyl-piperazinyl)-butane-1,4-dicarboxiamide]-N-[(8'-chrysenyl)-4-(1'-piperidinyl)-butane-1,4-dicarboxiamide].

11. A pharmaceutical composition, comprising:
(a) a compound having the formula

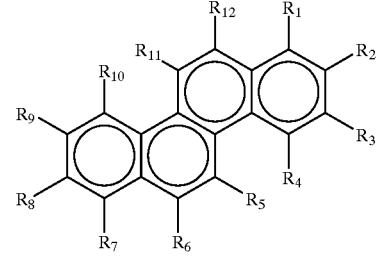

or a salt thereof;
where at least one of $R_1$–$R_{12}$ is —$R_{13}Z$, where $R_{13}$ is a substituted or unsubstituted amino or amido group having from 1–12 carbon atoms, and Z is a substituted or unsubstituted heterocyclic group having from 1–12 carbon atoms; and
where the remainder of $R_1$–$R_{12}$ are independently selected from the group consisting of hydrogen, substituted or unsubstituted amino or amido groups having from 1–12 carbon atoms, nitro, and substituted or unsubstituted hydrocarbyl groups having from 1–12 carbon atoms; and
(b) a pharmaceutically acceptable carrier.

12. The composition of claim 11, where $R_2$ is —$R_{13}Z$ and $R_1$ and $R_3$–$R_{12}$ are hydrogen.

13. The composition of claim 11, where $R_6$ is —$R_{13}Z$ and $R_1$–$R_5$ and $R_7$–$R_{12}$ are hydrogen.

14. The composition of claim 11, where $R_2$ and $R_8$ are each —$R_{13}Z$ and $R_1$, $R_3$–$R_7$, and $R_9$–$R_{12}$ are hydrogen.

15. The composition of claim 11, where $R_{13}$ has the formula —$NHR_{14}$—, where $R_{14}$ is a substituted or unsubstituted aliphatic group having from 2–6 carbon atoms.

16. The composition of claim 15, where $R_{14}$ is selected from the group consisting of —$CO(CH_2)_nCO$—, —$(CH_2)_m$—, and —$CO(CH_2)_qCHCH(CH_2)_rCO$—, where n is from 1–4, m is from 2–6, q is from 0–2, and r is from 0–2.

17. The composition of claim 11, where Z is selected from the group consisting of piperidinyl, piperazinyl, morpholinyl, thiomorpholinyl, pyrrolidinyl, pyridinyl, and thiophenyl.

18. The composition of claim 11, where the compound is selected from the group consisting of:
N-(2'-chrysenyl)4-(1'-piperidinyl)-butane-1,4-diamine;
N-[(6'-chrysenyl)-4-(4'N methyl-piperazinyl)-butane-1,4-diamine]-N-[(12'-chrysenyl)-4-(1'-piperidinyl)-butane-1,4-diamine; and N-[(2'-chrysenyl)-4-(1'-piperidinyl)-butane-1,4-diamine]-N-[(8'-chrysenyl)-4-(4'N methyl-piperazinyl)-butane-1,4-diamine.

19. The composition of claim 11, where the compound is selected from the group consisting of:
N-(2'-chrysenyl)-4-(4'N-methyl-piperazinyl)-butane-1,4-dicarboxiamide;
N-(2'-chrysenyl)-4-(4'N methyl-piperazinyl)-butane-1,4-diamine;
N-(2'-chrysenyl)-4-(4'N methyl-piperazinyl hydrochloride)-butane-1,4-dicarboxiamide;
N-(2'-chrysenyl)-3-(4'N methyl-piperazinyl)-propane-1,3-dicarboxiamide;
N-(2'-chrysenyl)-4-(1'-piperidinyl)-but-2-ene-1,4-dicarboxiamide;
N-(2'-chrysenyl)-4-(4'N-methyl-piperazinyl)-but-2-ene-1,4-dicarboxiamide; and
N-(6'-chrysenyl)-4-(4'N-methyl-piperazinyl)-but-2-ene-1,4-dicarboxiamide.

20. The composition of claim 11, where the compound is selected from the group consisting of:
N-(6'-chrysenyl)-4-(4'N methyl-piperazinyl)-butane-1,4-dicarboxiamide;
N-(6'-chrysenyl)-5-(4'N methyl-piperazinyl)-pentane-1,5-dicarboxiamide;
N-(2'-chrysenyl)-4-(4'-morpholinyl)-butane-1,4-dicarboxiamide;
N-(2'-chrysenyl)-4-(1'-thiomorpholinyl)-butane-1,4-dicarboxiamide;
N-(2'-chrysenyl)-4-(1'-pyrrolidinyl)-butane-1,4-dicarboxiamide; and
N-[(2'-chrysenyl)-4-(4'N methyl-piperazinyl)-butane-1,4-dicarboxiamide]-N-[(8'-chrysenyl)-4-(1'-piperidinyl)-butane-1,4-dicarboxiamide].

21. A method of inhibiting the growth of tumor cells, comprising the step of administering to a mammal an amount effective to inhibit tumor cell growth of a compound having the formula

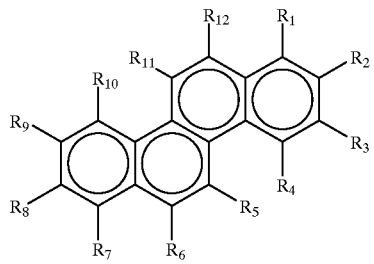

or a salt thereof;
where at least one of $R_1$–$R_{12}$ is —$R_{13}Z$, where $R_{13}$ is a substituted or unsubstituted amino or amido group having from 1–12 carbon atoms, and Z is a substituted or unsubstituted heterocyclic group having from 1–12 carbon atoms; and
where the remainder of $R_1$–$R_{12}$ are independently selected from the group consisting of hydrogen, substituted or unsubstituted amino or amido groups having from 1–12 carbon atoms, nitro, and substituted or unsubstituted hydrocarbyl groups having from 1–12 carbon atoms.

22. The method of claim 21, where $R_2$ is —$R_{13}Z$ and $R_1$ and $R_3$–$R_{12}$ are hydrogen.

23. The method of claim 21, where $R_6$ is —$R_{13}Z$ and $R_1$–$R_5$ and $R_7$–$R_{12}$ are hydrogen.

24. The method of claim 21, where $R_2$ and $R_8$ are each —$R_{13}Z$ and $R_1$, $R_3$–$R_7$, and $R_9$–$R_{12}$ are hydrogen.

25. The method of claim 21, where $R_{13}$ has the formula —$NHR_{14}$—, where $R_{14}$ is a substituted or unsubstituted aliphatic group having from 2–6 carbon atoms.

26. The method of claim 25, where $R_{14}$ is selected from the group consisting of $CO(CH_2)_nCO$—, —$(CH_2)_m$—, and —$CO(CH_2)_qCHCH(CH_2)_rCO$—, where n is from 1–4, m is from 2–6, q is from 0–2, and r is from 0–2.

27. The method of claim 21, where Z is selected from the group consisting of piperidinyl, piperazinyl, morpholinyl, thiomorpholinyl, pyrrolidinyl, pyridinyl, and thiophenyl.

28. The method of claim 21, where the compound is selected from the group consisting of:
N-(2'-chrysenyl)4-(1'-piperidinyl)-butane-1,4-diamine;
N-[(6'-chrysenyl)-4-(4'N methyl-piperazinyl)-butane-1,4-diamine]-N-[(12'-chrysenyl)-4-(1'-piperidinyl)-butane-1,4-diamine; and
N-[(2'-chrysenyl)-4-(1'-piperidinyl)-butane-1,4-diamine]-N-[(8'-chrysenyl)-4-(4'N methyl-piperazinyl)-butane-1,4-diamine.

29. The method of claim 21, where the compound is selected from the group consisting of:
N-(2'-chrysenyl)-4-(4'N-methyl-piperazinyl)-butane-1,4-dicarboxiamide;
N-(2'-chrysenyl)-4-(4'N methyl-piperazinyl)-butane-1,4-diamine;
N-(2'-chrysenyl)-4-(4'N methyl-piperazinyl hydrochloride)-butane-1,4-dicarboxiamide;
N-(2'-chrysenyl)-3-(4'N methyl-piperazinyl)-propane-1,3-dicarboxiamide;
N-(2'-chrysenyl)-4-(1'-piperidinyl)-but-2-ene-1,4-dicarboxiamide;
N-(2'-chrysenyl)-4-(4'N-methyl-piperazinyl)-but-2-ene-1,4-dicarboxiamide; and
N-(6'-chrysenyl)-4-(4'N-methyl-piperazinyl)-but-2-ene-1,4-dicarboxiamide.

30. The method of claim 21, where the compound is selected from the group consisting of:
N-(6'-chrysenyl)-4-(4'N methyl-piperazinyl)-butane-1,4-dicarboxiamide;
N-(6'-chrysenyl)-5-(4'N methyl-piperazinyl)-pentane-1,5-dicarboxiamide;
N-(2'-chrysenyl)-4-(4'-morpholinyl)-butane-1,4-dicarboxiamide;
N-(2'-chrysenyl)-4-(1'-thiomorpholinyl)-butane-1,4-dicarboxiamide;
N-(2'-chrysenyl)-4-(1'-pyrrolidinyl)-butane-1,4-dicarboxiamide; and N-[(2'-chrysenyl)-4-(4'N methyl-piperazinyl)-butane-1,4-dicarboxiamide]-N-[(8'-chrysenyl)-4-(1'-piperidinyl)-butane-1,4-dicarboxiamide].

31. A method of synthesizing a chrysene compound of claim 1, comprising the step of reacting an aromatic compound having a nitro group in the presence of samarium and a catalytic amount of iodine.

32. The method of claim 31, where the aromatic compound is a chrysene compound having a nitro group.

* * * * *